United States Patent
Heimbrock et al.

(10) Patent No.: US 6,341,398 B1
(45) Date of Patent: Jan. 29, 2002

(54) TRAUMA STRETCHER

(75) Inventors: Richard H. Heimbrock; Stephen R. Hamberg, both of Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 09/566,428

(22) Filed: May 8, 2000

Related U.S. Application Data

(60) Continuation-in-part of application No. 09/205,853, filed on Dec. 4, 1998, now Pat. No. 6,151,732, which is a division of application No. 08/895,847, filed on Jul. 17, 1997, now Pat. No. 5,996,149.
(60) Provisional application No. 60/138,341, filed on Jun. 9, 1999.

(51) Int. Cl.$^7$ ............................. A61G 1/00; C03B 42/02
(52) U.S. Cl. .............................. 5/601; 378/177; 378/209
(58) Field of Search ............................. 5/601; 378/177, 378/178, 179, 181, 182, 208, 209

(56) References Cited

U.S. PATENT DOCUMENTS

| | | |
|---|---|---|
| 1,768,769 A | 7/1930 | Kelley |
| 2,989,634 A | 6/1961 | Ould et al. |
| 3,774,045 A | 11/1973 | Trott |
| 3,795,815 A | 3/1974 | Weinstock et al. |
| 3,904,531 A * | 9/1975 | Barrett et al. ............... 250/444 |
| 3,968,374 A | 7/1976 | Schroeder |
| 4,193,148 A | 3/1980 | Rush |
| 4,464,780 A | 8/1984 | Ruiz |
| 4,538,293 A | 8/1985 | Cutter |
| 4,584,989 A | 4/1986 | Stith |
| 4,651,364 A * | 3/1987 | Hayton et al. ................. 5/601 |
| 4,893,323 A | 1/1990 | Cook, III |
| 4,905,266 A | 2/1990 | Kuck et al. |
| 4,916,725 A | 4/1990 | Quinter et al. |
| 4,926,457 A | 5/1990 | Poehner et al. |
| 4,947,418 A * | 8/1990 | Barr et al. ...................... 5/601 |
| 5,016,268 A | 5/1991 | Lotman |
| 5,138,646 A * | 8/1992 | Hubert et al. ............... 378/177 |
| 5,155,758 A | 10/1992 | Vogl |
| 5,255,303 A | 10/1993 | DeMaio et al. |
| 5,422,928 A | 6/1995 | Payne |
| 5,575,026 A | 11/1996 | Way et al. |
| 5,703,925 A * | 12/1997 | Wright ........................ 378/181 |
| 5,996,149 A * | 12/1999 | Heimbrock et al. ........... 5/601 |

FOREIGN PATENT DOCUMENTS

| | | |
|---|---|---|
| DE | 43 44 123 A1 | 6/1995 |
| FR | 2534 704 | 4/1984 |
| GB | 1 200 814 | 8/1970 |
| WO | WO 99 03396 | 1/1999 |

OTHER PUBLICATIONS

"ED II Emergency Department Stretcher", Stryker Medical Division product brochure, two pages, date unknown.
"921 InstaCare Trauma/Emergency Department Stretcher Modifications", Stryker Medical brochure, two pages, date unknown.

(List continued on next page.)

*Primary Examiner*—Michael F. Trettel
(74) *Attorney, Agent, or Firm*—Barnes & Thornburg

(57) ABSTRACT

In accordance with the present invention, a patient support apparatus includes a frame, a patient support deck coupled to the frame, a tray positioned below the patient support deck for supporting an x-ray cassette, and a lifting apparatus for lifting the tray toward the patient support deck. The lifting apparatus includes a shiftable member supported for translation relative to the frame in a longitudinal direction. A pair of links are coupled to the shiftable member. A first link of the pair of links has a first end pivotally coupled to the tray and a second end pivotally coupled to the shiftable member. A second link of the pair of links has a first end pivotally coupled to the frame and a second end pivotally coupled to the shiftable member. A handle is coupled to the frame for translating the shiftable member in the longitudinal direction to spread apart the links and lift the tray.

47 Claims, 5 Drawing Sheets

OTHER PUBLICATIONS

"Beta One X–Ray Bed", Beta Medical Products, Inc. brochure, two pages, date unknown.

"X–ray Trauma Stretcher", Beta Medical Products, Inc. brochure, two pages, date unknown.

"Patient Handling Systems", Stryker Medical Division brochure, two pages, date unknown.

"InstaCare/Emergency Stretcher Model 1000E", Stryker Medical brochure, two pages, date unknown.

"Advantages Series Trauma Stretcher Model 1002", Stryker Patient Handling brochure, three pages, Sep., 1993.

"Full Length X–Ray Trauma Stretcher Model 1020 Renaissance Series", Stryker Medical brochure, two pages, May, 1995.

"The Gemini Series", Hausted brochure, two pages, date unknown.

"Hausted Specialty Stretchers, The Unicare Series", Hausted product brochure, two pages,date unknown.

"Colson Trauma Stretcher", Colson brochure, one page, date unknown.

"530 ED/Trauma Stretcher", Midmark Corporation brochure, six pages, 1989.

"The Midmark 550/555 Stretcher", Midmark Corporation brochure, four pages, 1995.

"Here are just a few of the ways a C–100 cassette holder from Monee X–Ray Works can help you!", Monee X–Ray Works brochure, four pages, date unknown.

"Dual Control Critical Care Bed Model 2020", Stryker Medical brochure, two pages, date unknown.

\* cited by examiner

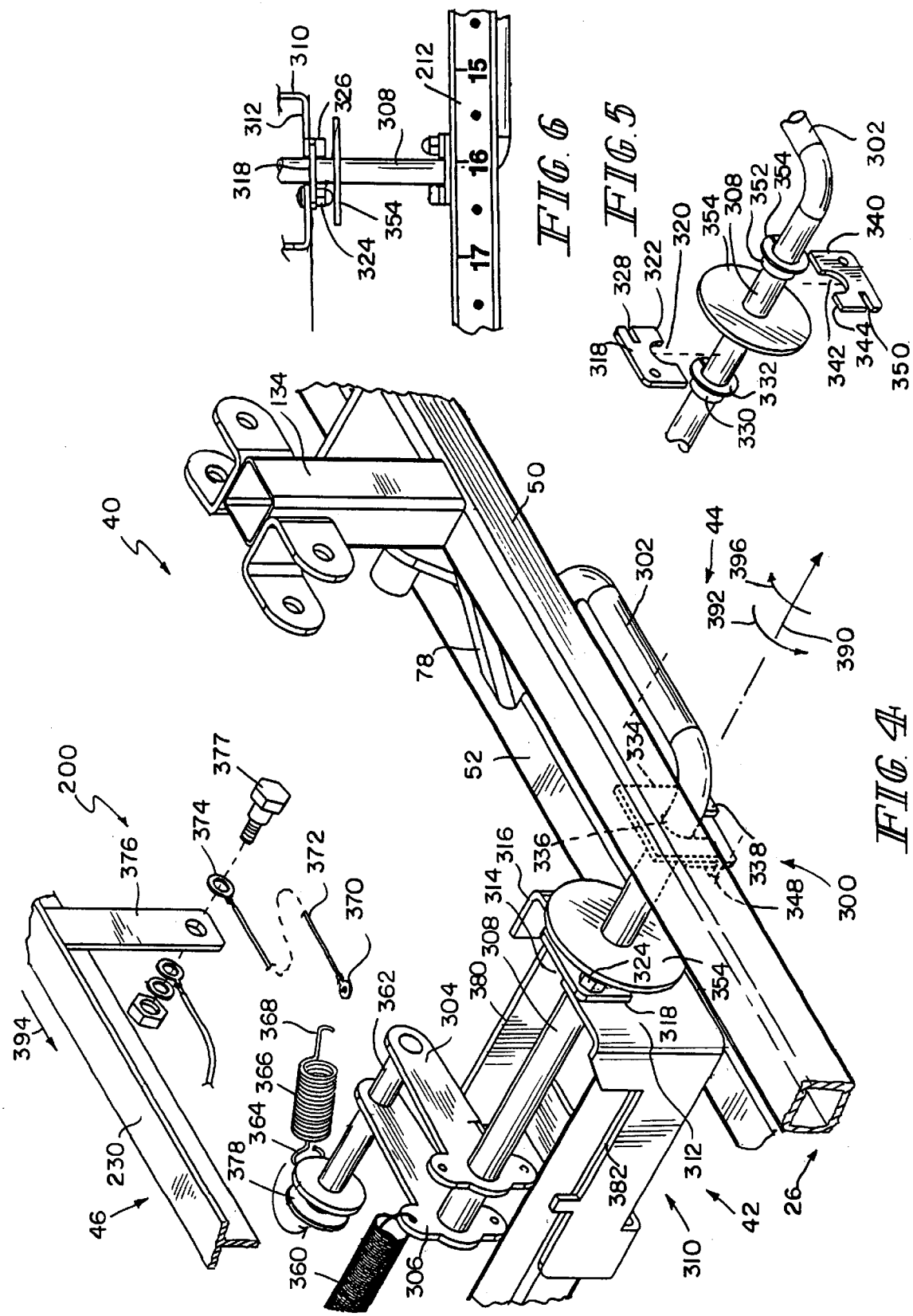

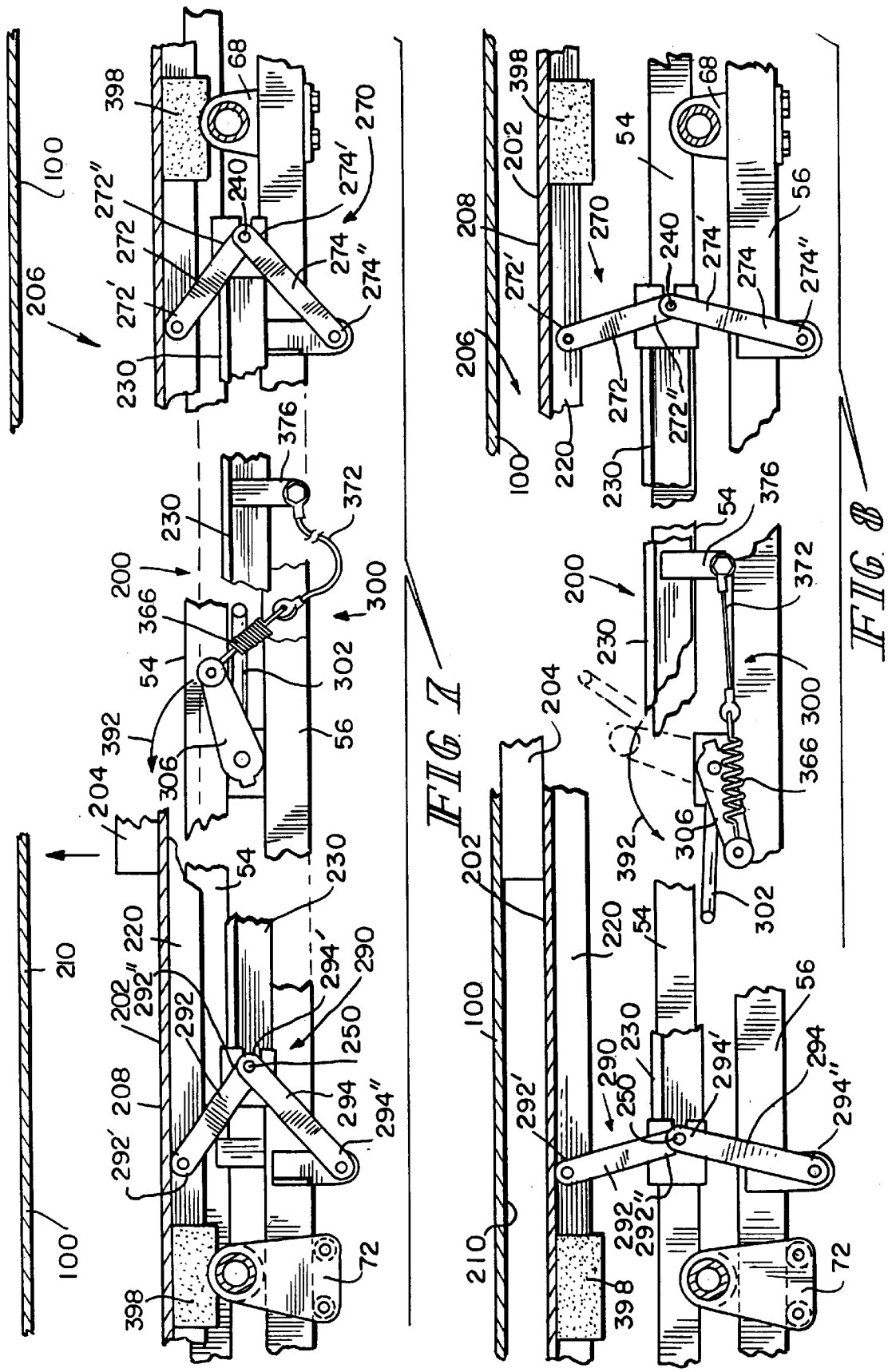

TRAUMA STRETCHER

The present application claims benefit of U.S. provisional patent application Serial No. 60/138,341, filed Jun. 9, 1999. The present application is also a continuation-in-part application of U.S. Ser. No. 09/205,853 filed Dec. 4, 1998, now issued as U.S. Pat. No. 6,151,732, which is a divisional application of U.S. Ser. No. 08/895,847 filed Jul. 17, 1997, now issued as U.S. Pat. No. 5,996,149.

BACKGROUND AND SUMMARY OF THE INVENTION

The present invention relates to a stretcher or hospital bed. More particularly, the present invention relates to a stretcher which facilitates taking x-rays of a patient located on a support surface of the stretcher.

Although the term "stretcher" is used throughout the specification of the present application, it is understood that the novel features of the invention may be incorporated into any type of bed or patient support device.

Stretchers or beds which include structures for holding an x-ray cassette are known. See, for example, U.S. Pat. Nos. 1,768,769; 3,774,045; 4,193,148; 4,584,989; 4,651,364; 4,893,323; 4,905,266; 4,916,725; 4,926,457; 4,947,418; 5,155,758; 5,255,303; and 5,422,928.

During an emergency or trauma situation, it is important to have the maximum flexibility in placement of an x-ray cassette relative to a patient. In addition, it is important to provide the best x-ray image possible on the x-ray cassette. Typically, x-ray radiation spreads out or magnifies as the distance increases between the patient and the x-ray cassette. Therefore, it is desirable to place the x-ray cassette as close to the patient as possible.

The present invention is related to U.S. Pat. No. 5,996,149, which is incorporated herein by reference. The present invention provides an improved x-ray tray located adjacent a patient support surface of the stretcher. The improved x-ray tray permits the x-ray cassette to be loaded at substantially any horizontal location below the patient support deck by sliding the cassette onto the tray using the hands. Enough room is provided between the frame and the patient support deck for hands to pass between. After the x-ray cassette is loaded on the x-ray tray at a desired horizontal location below the patient, the x-ray tray can then be lifted upwardly by a lifting apparatus to position the x-ray cassette adjacent a bottom surface of the patient support deck to improve x-ray imaging on the cassette.

In accordance with the present invention, a patient support apparatus includes a frame, a patient support deck coupled to the frame, a tray positioned below the patient support deck for supporting an x-ray cassette, and a lifting apparatus for lifting the tray toward the patient support deck. The lifting apparatus includes a shiftable member supported for longitudinal translation relative to the frame. A pair of links are coupled to the shiftable member. A first link of the pair of links has a first end pivotally coupled to the tray and a second end pivotally coupled to the shiftable member. A second link of the pair of links has a first end pivotally coupled to the frame and a second end pivotally coupled to the shiftable member. The shiftable member is movable in a longitudinal direction to spread apart the links and lift the tray. A handle may preferably be provided for moving the shiftable member.

According to another feature of the present invention, the x-ray tray moves only vertically relative to the frame between a lower first position spaced apart from the deck to permit loading of an x-ray cassette on the x-ray tray and an elevated second position located closer to the deck. In accordance with a further feature of the present invention, the x-ray tray includes flanges at opposite ends which are configured to engage cross members coupled to the frame to hold the x-ray tray in the same horizontal position relative to the frame during movement of the x-ray tray.

According to another feature of the present invention, the x-ray tray extends below substantially the entire length dimension of the deck. In accordance with a still another feature of the present invention, the x-ray tray includes a non-slip top surface for engaging the x-ray cassette. According to a further feature of the present invention, the handle is movable to a storage position located under the frame, and the handle is spring-biased toward its storage position.

In accordance with still another feature of the present invention, the handle is pivotally coupled to the frame, and the lifting apparatus includes a spring having a first end coupled to the handle and a second end coupled to the shiftable member to lift the x-ray tray upwardly to its elevated second position when the handle is rotated relative to the frame from a first storage position to a second x-ray position.

According to a further feature of the present invention, the lifting apparatus includes a shaft coupled to the handle and an arm having a first end coupled to the shaft and a second end coupled to the first end of the spring. In accordance with a still further feature of the present invention, the arm is configured such that rotation of the handle to the second x-ray position moves the arm over center to cause the spring to bias the x-ray tray toward its elevated second position. According to another feature of the present invention, the spring is configured to hold the x-ray tray in its elevated second position to urge the x-ray cassette against a bottom surface of the deck regardless of the thickness of an x-ray cassette supported on the x-ray tray.

Additional features and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 4 is a partial perspective view of the lifting apparatus of FIGS. 2 and 3, showing a handle pivotally coupled to the frame, a shaft coupled to the handle, an arm extending from the shaft, and a spring having one end coupled to the arm and a second end coupled to a cable secured to the shiftable member, FIG. 5 is a partial perspective view showing the handle coupled to the shaft, and further showing the details of mounting of the shaft to the frame, FIG. 6 is a partial plan view showing the handle pivotally coupled to the frame, the shaft coupled to the handle, and indicia secured to the frame for indicating the position of the x-ray cassette relative to the frame, FIG. 7 is a sectional view taken along lines 7—7 of FIG. 1, illustrating the x-ray tray positioned below the deck, the x-ray tray shown in its lowered first position to allow placement of an x-ray cassette thereon, a plurality of linkages coupled between the tray and to the frame, a shiftable member coupled to said linkages for translation in a longitudinal direction, the handle rotatably coupled to the frame, the arm coupled to the handle, and the spring having a first end coupled to the arm and a second end coupled to the cable secured to the shiftable member, and FIG. 8 is a sectional view similar to the FIG. 7, illustrating the x-ray tray moved to its upwardly extended x-ray position to hold the x-ray cassette against a bottom surface of the patient support deck.

DETAILED DESCRIPTION OF THE DRAWINGS

The present invention will be described in conjunction with a trauma stretcher, but it will be understood that the same may be used in conjunction with any patient support apparatus, such as a surgical table, a hospital bed, an ambulatory chair and so on. Also, although the x-ray tray lifting apparatus of the present invention is used to lift an x-ray cassette against a bottom surface of a patient support deck of a trauma stretcher, it may very well be used to lift a different accessory. As a result, the x-ray tray lifting apparatus of the present invention is not to be limited to be used with a trauma stretcher or an x-ray cassette.

Figure 1:
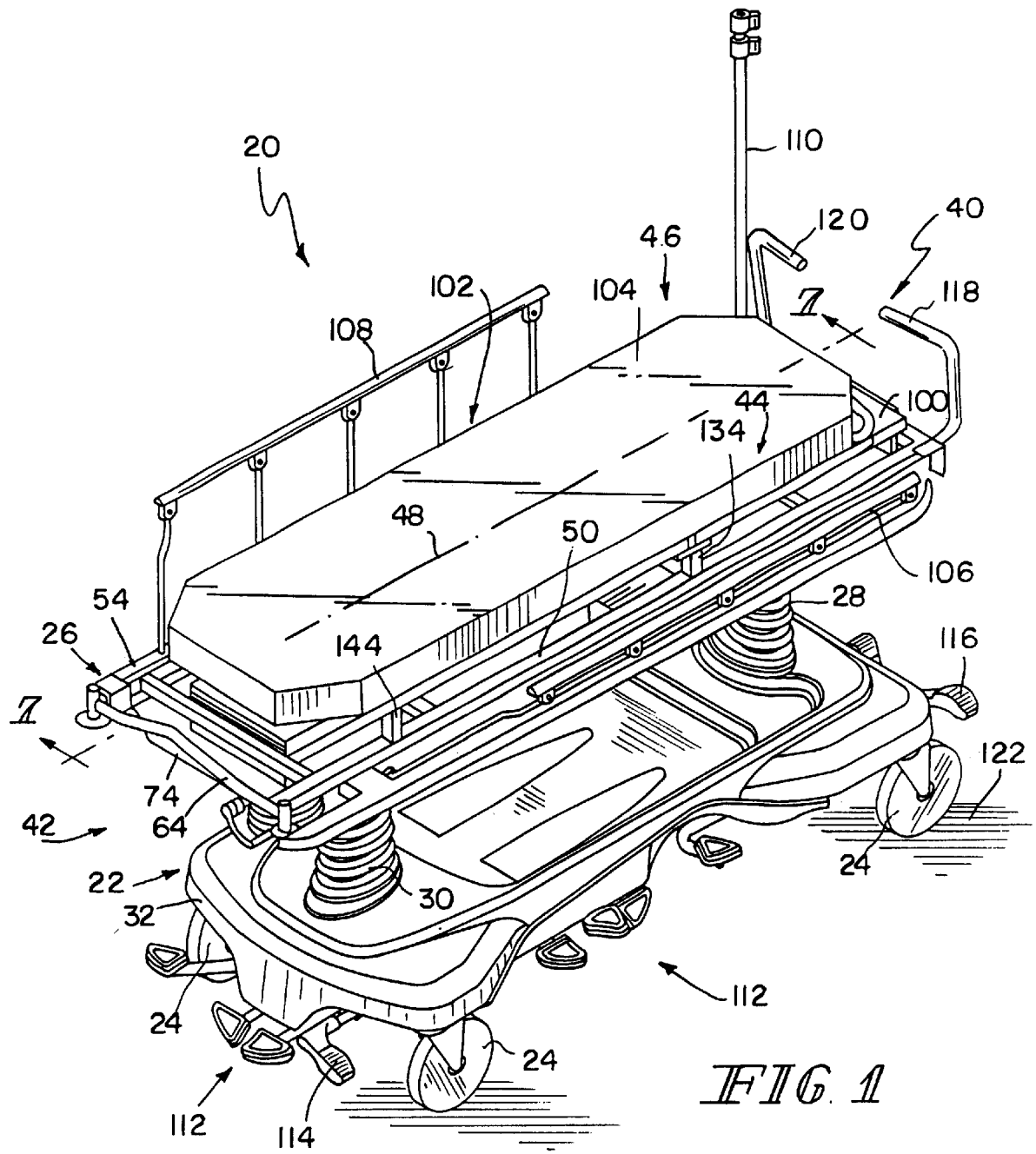
FIG. 1 is a perspective view of a trauma stretcher including a base supported on casters, an upper frame coupled to the base by front and rear frame lifting mechanisms, a patient support deck coupled to the frame, an x-ray tray located beneath the patient support deck for supporting an x-ray cassette, and an x-ray tray lifting apparatus in accordance with the present invention for lifting the x-ray tray to an elevated second position adjacent to the patient support deck.

Referring to FIG. 1, a trauma stretcher 20 in accordance with the present invention includes a base 22 supported on casters 24, an upper frame 26 coupled to the base 22 by a pair of frame lifting mechanisms 28, 30, a shroud 32 covering the base 22, a head end 40, a foot end 42, an elongated first side 44, an elongated second side 46, and a longitudinal axis 48. As used in this description, the phrase "head end 40" will be used to denote the end of any referred-to object that is positioned to lie nearest the head end 40 of the stretcher 20, and the phrase "foot end 42" will be used to denote the end of any referred-to object that is positioned to lie nearest the foot end 42 of the stretcher 20. Likewise, the phrase "first side 44" will be used to denote the side of any referred-to object that is positioned to lie nearest the first side 44 of the stretcher 20 and the phrase "second side 46" will be used to denote the side of any referred-to object that is positioned to lie nearest the second side 46 of the stretcher 20.

Figure 3:
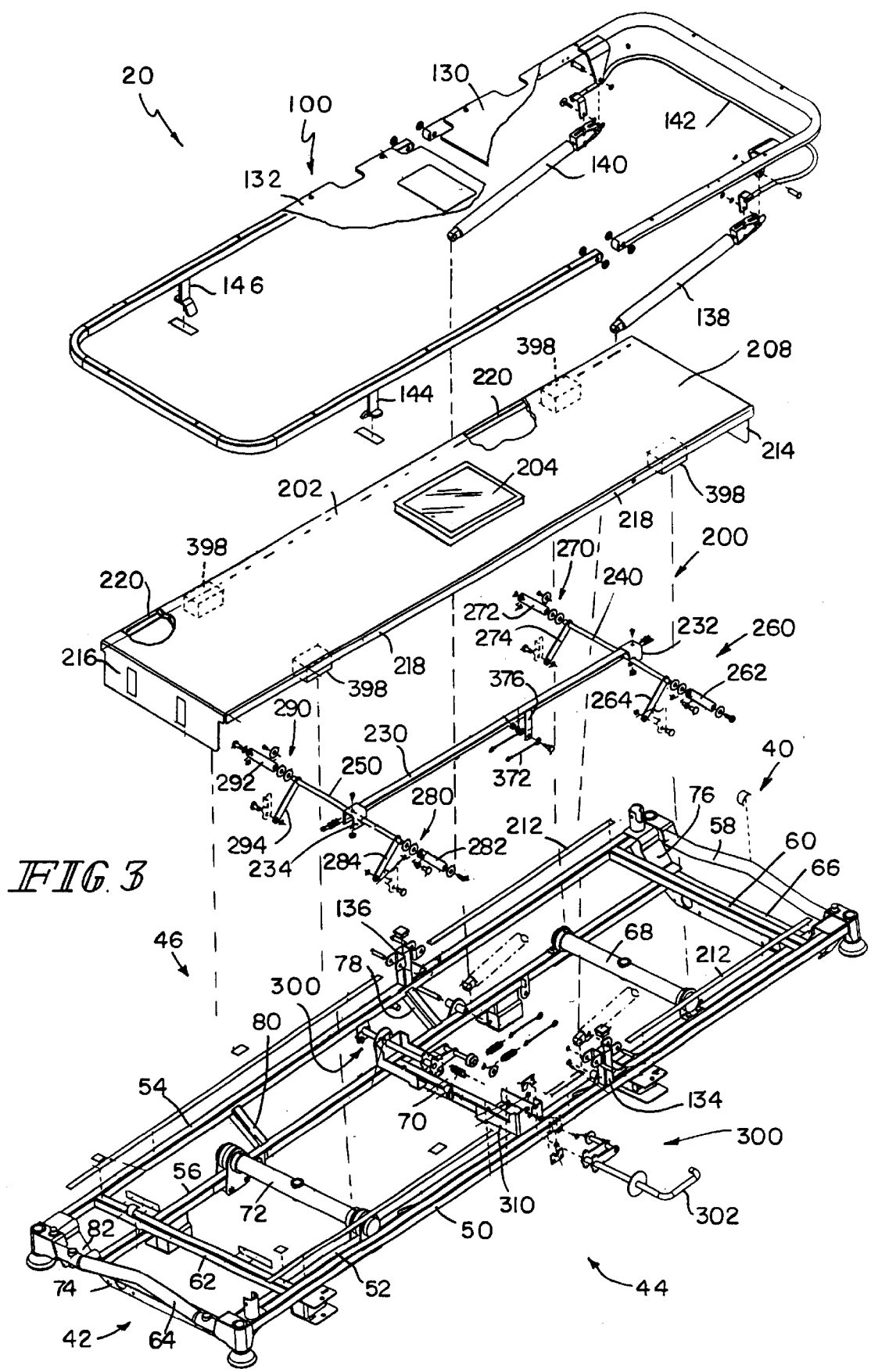
FIG. 3 is an exploded perspective view, with portions broken away, of the trauma stretcher of FIG. 1, showing a patient support deck, the x-ray tray having flanges at opposite ends, the x-ray tray lifting apparatus of FIG. 2 and the frame.

As shown in FIG. 3, the frame 26 includes upper and lower side rails 50, 52 on the first side 44 of the stretcher 20, and upper and lower side rails 54, 56 on the second side 46 of the stretcher 20. The upper side rails 50, 54 are held in laterally spaced apart relation by a plurality of generally horizontally extending cross members 58, 60, 62 64. The lower side rails 52, 56 are held in laterally spaced apart relation by a plurality of generally horizontally extending cross members 66, 68 70, 72 74. The upper and lower side rails 50, 54 and 52, 56 are held in vertically spaced apart relation by a plurality of generally vertically extending strut members 76, 78, 80, 82. The frame lifting mechanisms 28, 30 are coupled to the cross members 68, 72 secured to the lower side rails 64, 66. The frame lifting mechanisms 28, 30 respectively control the vertical position of the head and foot ends 40, 42 of the frame 26. Besides lifting and lowering the frame 26 relative to the base 26, the frame lifting mechanisms 28, 30 tilt the frame 26 relative to the base 22 between a Trendelenburg position where the head end 40 of the frame 26 is below the foot end 42, and a reverse Trendelenburg position where the head end 40 of the frame 26 is above the foot end 42.

A patient support deck 100 is supported by the upper side rails 50, 54 of the frame 26. A mattress 102 having an upwardly-facing patient support surface 104 is carried by the deck 100. A pair of side guard rails 106, 108 are mounted on the opposite sides 44, 46 of the deck 78. An IV pole 110 for holding solution containers or other objects at a position elevated above the deck 100 is pivotably attached to the frame 26. The deck 100 is illustratively made from radiolucent material to permit x-rays to pass through the deck 100. A suitable material for the deck 100 may be Formica having less than one millimeter coating of aluminum.

Several foot pedals 112 are pivotably coupled to the base 22 and are coupled to the frame lifting mechanisms 28, 30 to control the vertical positions of the head and foot ends 40, 42 of the frame 26. In addition, a brake pedal 114 is coupled to the base 22 near the foot end 42 to control the braking of the casters 24. A brake-steer butterfly pedal 116 is coupled to the base 22 near the head end 40 to control both the braking of the casters 24, and the release of the braked casters 24. Each of the foot pedals 112, brake pedal 114, and brake-steer pedal 116 extends outwardly from the base 22. Push bars 118, 120 are pivotally mounted to the head end 40 of the frame 26 to enable the caregiver to manually push the stretcher 20 over a floor 122.

Referring to FIGS. 1 and 3, the deck 100 includes a head section 130 and a foot section 132. The head section 130 is pivotally coupled to standoffs 134, 136 mounted on the upper side rails 50, 54 for movement between a lowered horizontal position shown in FIG. 1 and a raised inclined position (not shown). Likewise, the foot section 132 is pivotally coupled to the standoffs 134, 136 for movement between a lowered horizontal position shown in FIG. 1 and a raised inclined position (not shown). A pair of gas cylinders 138, 140 are coupled to the opposite sides 44, 46 of the head section 130. An actuator 142 releases the gas cylinders 138, 140 to permit the head section 130 to pivot about the standoffs 134, 136. The gas cylinders 124. 126 lock the head section 130 in place at the desired angle when the actuator 142 is freed. A pair of legs 144, 146 are coupled to the foot section 132 near the foot end 42 as shown in FIG. 3. The standoffs 134, 136, the gas cylinders 138, 140 and the legs 144, 146 cooperate to hold the deck 100 in a spaced apart relationship with the upper side rails 50, 54.

In accordance with the present invention, the stretcher 20 includes an x-ray tray lifting apparatus 200. The x-ray tray lifting apparatus 200 includes an x-ray tray 202 configured to support an x-ray cassette 204. As previously indicated, the deck 100 is spaced apart from the upper side rails 50, 54 to form a space 206 for receiving the x-ray tray 202 as shown in FIGS. 7 and 8. The x-ray tray 202 is centered on the stretcher 20, and extends substantially below the entire length and width dimension of the deck 100. This facilitates placement of an x-ray cassette 204 at any desired location on the x-ray tray 202. A top surface 208 of the x-ray tray 202 may be covered with a non-slip pad having a texture to prevent sliding of the x-ray cassette 204 when the stretcher 20 is tilted to Trendelenburg or reverse Trendelenburg positions.

Figure 2:
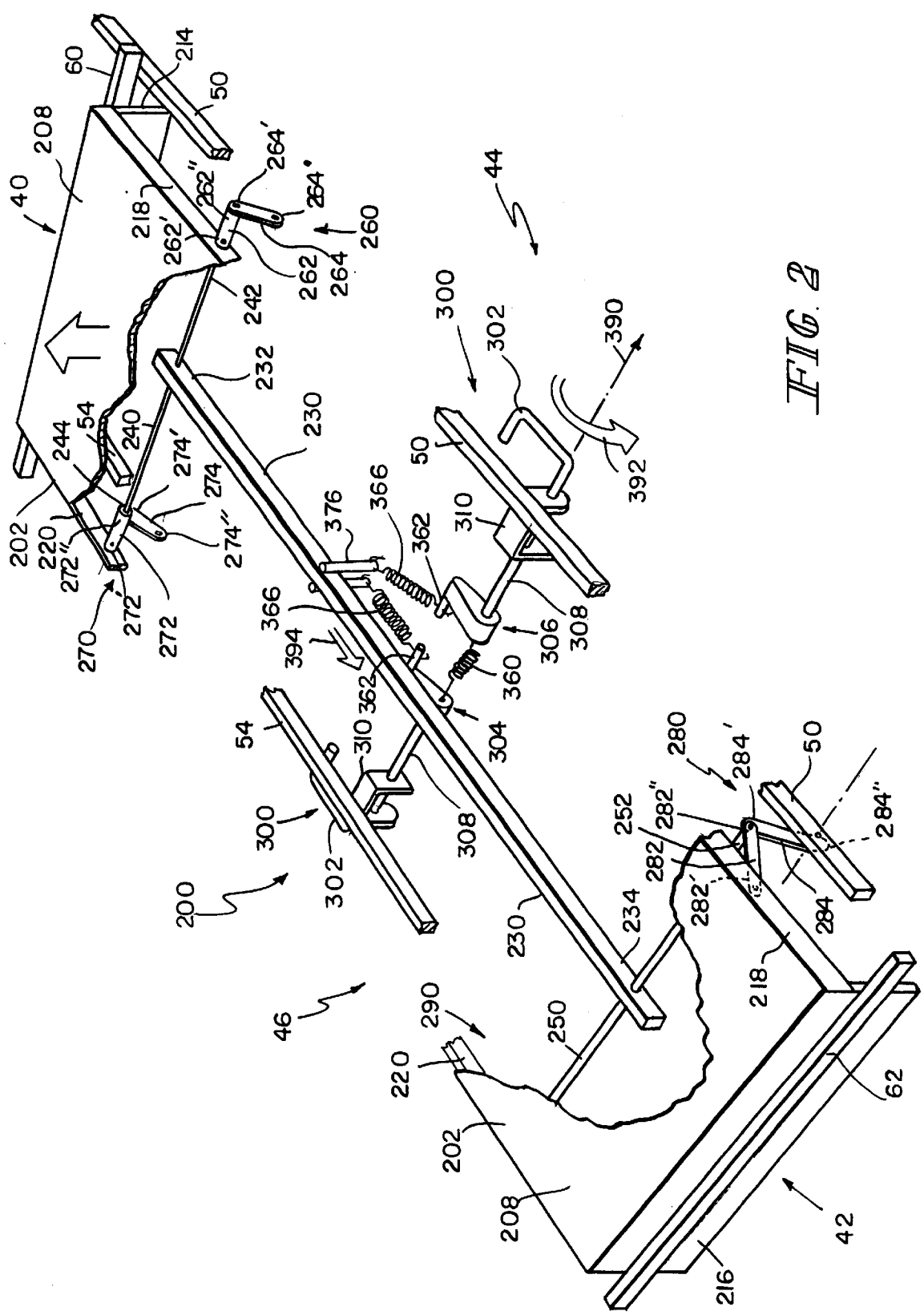
FIG. 2 is a partial perspective view of the x-ray tray lifting apparatus in schematic representation with portions broken away, showing an x-ray tray having flanges at opposite ends configured to engage first and second cross members coupled to the frame, a plurality of linkages coupled between the x-ray tray and the frame, a shiftable member coupled to said linkages for translation in a longitudinal direction, a handle pivotally coupled to the frame, a shaft coupled to the handle for rotation therewith, an arm coupled to the shaft, and a spring having a first end coupled to the arm and a second end coupled to the shiftable member to lift the x-ray tray upwardly to its elevated second position when the handle is pulled outwardly from a first storage position under the frame and rotated relative to the frame to a second x-ray position, the handle is then pushed inwardly under the frame.

The x-ray tray 202 is supported for movement between (a) a lowered cassette loading position illustrated in FIG. 7 to allow placement of an x-ray cassette 204 on the x-ray tray 202, and (b) an elevated x-ray position to move the x-ray cassette 204 against a bottom surface 210 of the deck 100 as illustrated in FIG. 8. The quality of x-ray images on the x-ray cassette 204 is improved by positioning the x-ray cassette 204 close to the bottom surface 210 of the deck 100. As shown in FIG. 6, the top surfaces of the upper side rails 50, 54 are marked with indicia 212 to help the caregiver to accurately place the x-ray cassette 204 on the tray 202. As schematically shown in FIG. 2, the tray 202 includes laterally extending end flanges 214, 216 at opposite ends 40, 42 which are configured to engage the cross bars 60, 62 coupled to the upper side rails 50, 54 to maintain the tray 202 in the same horizontal position relative to the deck 100 as the tray 202 moves up and down. The tray 202 further includes longitudinally extending side flanges 218, 220 on opposite sides 44, 46 thereof.

As shown in FIGS. 2 and 3, the x-ray lifting apparatus 200 further includes a shiftable member 230 supported for translation relative to the frame 26 in the longitudinal direction 48. A pair of transverse pivot rods 240, 250 are rotatably coupled to opposite ends 232, 234 of the shiftable member 230. The pivot rods 240, 250 are coupled to the x-ray tray 202 and the upper side rails 50, 54 by four linkages a pair of linkages 260, 270 adjacent to the head end 40 of the stretcher 20 and a pair of linkages 280, 290 adjacent the foot end 42 of the stretcher 20. The linkages 260, 270 couple opposite ends 242, 244 of the pivot rod 240 to the side flanges 218, 220 of the tray 202 and the upper side rails 50, 54 respectively. The linkages 280, 290, on the other hand, couple opposite ends 252, 254 of the pivot rod 250 to the side flanges 218, 220 of the x-ray tray 202 and the upper side rails 50, 54 respectively.

Referring to FIGS. 2, 3, 7 and 8, the linkage 260 includes (a) an upper link 262 having an upper end 262' pivotally coupled to the side flange 218 of the tray 202 and a lower end 262" pivotally coupled to the first end 242 of the pivot rod 240, and (b) a lower link 264 having an upper end 264' pivotally coupled to the first end 242 of the pivot rod 240 and a lower end 264" pivotally coupled to the upper side rail 50. The linkage 270 includes (a) an upper link 272 having an upper end 272' pivotally coupled to the side flange 220 of the tray 202 and a lower end 272" pivotally coupled to the second end 244 of the pivot rod 240, and (b) a lower link 274 having an upper end 274' pivotally coupled to the second end 244 of the pivot rod 240 and a lower end 274" pivotally coupled to the upper side rail 54.

On the other hand, the linkage 280 includes (a) an upper link 282 having an upper end 282' pivotally coupled to the side flange 218 of the tray 202 and a lower end 282" pivotally coupled to the first end 252 of the pivot rod 250, and (b) a lower link 284 having an upper end 284' pivotally coupled to the first end 252 of the pivot rod 250 and a lower end 284" pivotally coupled to the upper side rail 50. The linkage 290 includes (a) an upper link 292 having an upper end 292' pivotally coupled to the side flange 220 of the tray 202 and a lower end 292" pivotally coupled to the second end 254 of the pivot rod 250, and (b) a lower link 294 having an upper end 294' pivotally coupled to the second end 254 of the pivot rod 250 and a lower end 294" pivotally coupled to the upper side rail 54.

It will be seen from FIGS. 2, 3, 7 and 8 that the shiftable member 230, the two pivot rods 240, 250, the two upper links 262, 272 coupled to the pivot rod 240 adjacent to the head end 40 of the stretcher 20, the two upper links 282, 292 coupled to the pivot rod 250 adjacent to the foot end 42 of the stretcher 20 and the x-ray tray 202 form a first parallelogram arrangement. Likewise, the shiftable member 230, the two pivot rods 240, 250, the two lower links 264, 274 coupled to the pivot rod 240 adjacent to the head end 40 of the stretcher 20, the two lower links 284, 294 coupled to the pivot rod 250 adjacent to the foot end 42 of the stretcher 20 and the upper side rails 50, 54 form a second parallelogram arrangement. The upper links 262, 272, 282 and 292 and the lower links 264, 274, 284 and 294 spread apart when the shiftable member 230 is translated toward the foot end 42 of the stretcher 20 to lift the tray 202 toward the deck 100. On the other hand, the upper links 262, 272, 282 and 292 and the lower links 264, 274, 284 and 294 collapse when the shiftable member 230 is translated toward the head end 40 of the stretcher 20 to lower the tray 202.

As will be seen from FIGS. 2 and 3, the x-ray tray lifting apparatus 200 includes two actuating mechanisms 300, one on each side 44, 46 of the deck 100. Each actuating mechanism 300 is coupled to the shiftable member 230 for translating the shiftable member 230 toward the foot end 42 of the stretcher 20 to lift the tray 202 to its elevated second position to hold the cassette 204 against the bottom surface 210 of the deck 100 as shown in FIG. 8. The two actuating mechanisms 300 are mirror images of each other. The actuating mechanism 300 adjacent to the first side 44 of the stretcher 20 will be described below with reference to FIG. 4. The description of construction and operation of the other actuating mechanism 300 adjacent to the second side 46 of the stretcher 20 is the same.

The actuating mechanism 300 includes a handle 302 pivotally coupled to the frame 26. The handle 302 is rotatable between (a) a first storage position under the upper side rail 50 and pointing toward the head end 40 of the stretcher 20 as shown in FIGS. 4 and 7, and (b) a second x-ray position under the upper side rail 50, but pointing toward the foot end 42 of the stretcher 20 as shown in FIG. 8. The rotation of the handle 302 from a first storage position pointing toward the head end 40 of the stretcher 20 to a second x-ray position pointing toward the foot end 42 of the stretcher 20 moves the tray 202 from a lowered first position spaced apart from the deck 100 as shown in FIG. 7 to an elevated second position close to the deck 100 as shown in FIG. 8.

As shown in FIGS. 4 and 5, the handle 302 is coupled to a pair of generally triangular-shaped arms or lobes 304, 306 by a shaft 308. The shaft 308 is coupled to a bracket 310 mounted on the lower side rail 52. The bracket 310 includes a generally vertically extending outer wall 312 having an upwardly facing semicircular opening 314 near its upper edge 316 for receiving the shaft 308. A bushing plate 318 having a downwardly facing semicircular opening 320 near its lower edge 322 for receiving the shaft 308 is secured to the outer wall 312 of the bracket 310 by a screw 324. The generally vertically extending outer wall 312 of the bracket 310 includes an outwardly extending tab 326 (shown in FIG. 6) configured for reception in a generally horizontally extending slot 328 formed in the bushing plate 318 to facilitate assembly of the bushing plate 318 to the outer wall 312 of the bracket 310. A bushing 330 having a collar 332 is mounted on the shaft 308 to reduce friction and noise.

As shown in FIGS. 4 and 5, a generally vertically extending plate 334 having a downwardly facing semicircular opening 336 near its lower edge 338 for receiving the shaft 308 is secured to the inner wall of the upper side rail 50. A bushing plate 340 having an upwardly facing semicircular opening 342 near its upper edge 344 for receiving the shaft 308 is secured to the generally vertically extending plate 334 by a screw 346 (not shown). The generally vertically extending plate 334 includes an inwardly extending tab 348 configured for reception in a generally horizontally extending slot 350 formed in the bushing plate 340 to facilitate assembly of the bushing plate 340 to the generally vertically extending plate 334 coupled to the upper side rail 50. A bushing 352 having a collar 354 is mounted on the shaft 308 to reduce friction and noise.

As shown in FIG. 5, a wheel 354 coupled the shaft 308 is positioned between the two bushing collars 332, 354 so that (a) when the handle 302 is pushed inwardly to a position under the upper side rail 50, the wheel 356 engages the inner collar 332, and (b) when the handle 302 is pulled outwardly to clear the upper side rail 50, the wheel 356 engages the outer collar 350. It will be seen from FIG. 5 that the two collars 332, 354 are positioned outwardly with respect to the corresponding bushing plates 318, 340 to allow the handle 302 to be pushed in to a storage position under the upper side rail 50, and pulled out to clear the upper side rail 50 to permit rotation of the handle 302. A spring 360 is coupled between the two generally triangular-shaped inner lobes 306 of the actuating mechanisms 300 to bias the two handles 302 inwardly toward the center of the stretcher 20 to their respective storage positions under the upper side rails 50, 54.

The actuating mechanism 300 further includes a shaft 362 coupled to the two generally triangular-shaped lobes 304, 306. A first end 364 of a spring 366 is coupled to the shaft 362. A second end 368 of the spring 366 is coupled to a first end 370 of a cable 372. A second end 374 of the cable 372 is coupled by screw 377 to a downwardly extending arm 376 attached to the shiftable member 230. A washer 378 is mounted on the shaft 362 to retain the spring 366 on the shaft 362. Laterally extending walls 380, 382 of the bracket 310 are configured to engage the generally triangular-shaped lobes 304, 306 to limit the motion of the handle 302 in either direction.

In operation, when the handle 302 is extended outwardly in the direction of arrow 390 to clear the upper side rail 50 and rotated in the direction of arrow 392 toward the foot end 42 of the stretcher 20, the generally triangular-shaped lobes 304, 306 also rotate in the direction of arrow 392 to stretch the spring 366. This causes the spring 366 to pull the downwardly extending arm 376 attached to the shiftable member 230 toward the foot end 42 of the stretcher 20 in the direction of arrow 394. As shown in FIG. 8, the upper links 262, 272, 282 and 292 and the lower links 264, 274, 284 and 294 spread apart when the shiftable member 230 is translated toward the foot end 42 of the stretcher 20 to lift the tray 202 toward the deck 100 to press an x-ray cassette 204 supported by the tray 202 against the bottom surface 210 of the deck 100. The handle 302 is then pushed inwardly to a position under the upper side rail 50, but pointing toward the foot end 42 of the stretcher 20. When the handle 302 is thus extended outwardly to clear the upper side rail 50 and rotated toward the foot end 42 of the stretcher 20 in the direction of the arrow 392, the spring 366 passes its over-the-center position to bias the tray 202 upwardly toward its elevated second position as shown in FIG. 8.

To lower the tray 202, the handle 302 is extended outwardly in the direction of arrow 390 to clear the upper side rail 50, and rotated toward the head end 40 of the stretcher 20 in the direction of arrow 396. Rotation of the handle 302 in the direction of the arrow 396 relaxes the spring 366, and allows the tray 202 to move to its lowered first position shown in FIG. 7 by virtue of gravity. The tray 202 includes cushions or pads 398 shown in FIG. 3 which are configured to engage cross-members 68, 72 or other portions of the frame 26 to cushion downward movement of the tray 202 and reduce noise. It will be noted that either handle 302 may be operated to lift the tray 202. Also, the two handles 302 are operable independently of each other.

The sum of the distances between the upper and lower ends 262' and 262", 272' and 272", 282' and 282" and 292' and 292" of the upper links 262, 272, 282 and 292 and the upper and lower ends 264' and 264", 274' and 274", 284' and 284" and 294' and 294" of the corresponding lower links 264, 274, 284 and 294 is greater than the vertical distance between the deck 100 and the upper side rails 50, 54 to ensure that an x-ray cassette 204 supported on the tray 202 is pressed against the bottom surface 210 of the deck 100 regardless of the thickness of the x-ray cassette 204. This relationship also ensures that the tray 202 moves to its lowered first position shown in FIG. 7 by virtue of gravity and that the tray 202 does not get hung up in its elevated second position shown in FIG. 8 when the rotation of the handle 302 toward the head end 40 of the stretcher 20 relaxes the spring 366. All the links 262, 264, 272, 274, 282, 284, 292 and 294 in the illustrated embodiment are the same length.

Although the invention has been described in detail with reference to certain preferred embodiments, additional variations and modifications exist within the scope and spirit of the invention as described and defined in the following claims.

What is claimed is:

1. A lifting apparatus for an x-ray tray positioned below a patient support deck coupled to a frame, the lifting apparatus comprising:

a shiftable member supported for translation relative to the frame in a longitudinal direction, a pair of links coupled to the shiftable member, a first link of the pair of links having a first end pivotally coupled to the tray and a second end pivotally coupled to the shiftable member, a second link of the pair of links having a first end pivotally coupled to the frame and a second end pivotally coupled to the shiftable member, and the shiftable member being movable in the longitudinal direction to spread apart the links and lift the tray toward the patient support deck.

2. The apparatus of claim 1, wherein the x-ray tray moves only vertically relative to the frame between a lower first position spaced apart from the deck to permit loading of an x-ray cassette on the x-ray tray and an elevated second position located closer to the deck.

3. The apparatus of claim 2, comprising first and second cross members coupled to the frame, the x-ray tray including flanges at opposite ends configured to engage the first and second cross members coupled to the frame to hold the x-ray tray in the same horizontal position relative to the frame during movement of the x-ray tray.

4. The apparatus of claim 1, wherein the deck has a length dimension, and wherein the x-ray tray extends below substantially the entire length dimension of the deck.

5. The apparatus of claim 1, wherein the x-ray tray includes a non-slip top surface for engaging the x-ray cassette.

6. The apparatus of claim 1, including a handle for moving the shiftable member, the handle being movable to a storage position located under the frame.

7. The apparatus of claim 6, wherein the handle is spring-biased to the storage position.

8. The apparatus of claim 1, including a handle pivotably coupled to the frame, the apparatus further comprising a spring having a first end coupled to the handle and a second end coupled to the shiftable member to lift the x-ray tray upwardly to its elevated second position when the handle is rotated relative to the frame from a first storage position to a second x-ray position.

9. The apparatus of claim 8, further comprising a shaft coupled to the handle, and an arm having a first end coupled to the shaft and a second end coupled to the first end of the spring.

10. The apparatus of claim 9, wherein the arm is configured such that rotation of the handle to the second x-ray position moves the arm over center to cause the spring to bias the x-ray tray toward its elevated second position.

11. The apparatus of claim 1, further comprising a spring coupled between a handle and the shiftable member, the spring being configured to hold the x-ray tray in an elevated position to urge an x-ray cassette supported on the x-ray tray against a bottom surface of the deck regardless of the thickness of the x-ray cassette supported on the x-ray tray.

12. The apparatus of claim 1, wherein the sum of the distances between the first and second ends of the first and second links is greater than the distance between the deck and the frame so as to enable the lifting apparatus to hold the x-ray cassette against a bottom surface of the deck regardless of the thickness of an x-ray cassette supported on the x-ray tray.

13. A patient support apparatus comprising:
a frame,
a patient support deck coupled to the frame,
an x-ray tray located below the deck and being configured to receive an x-ray cassette,
a shiftable member having first and second ends,
a first pair of links coupled to the first end of the shiftable member, each first pair of links including a first link having a first end pivotally coupled to the x-ray tray and a second end pivotally coupled to the first end of the shiftable member, each first pair of links including a second link having a first end pivotally coupled to the frame and a second end pivotally coupled to the first end of the shiftable member,
a second pair of links coupled to the second end of the shiftable member, each second pair of links including a first link having a first end pivotally coupled to the x-ray tray and a second end pivotally coupled to the second end of the shiftable member, each second pair of links including a second link having a first end pivotally coupled to the frame and a second end pivotally coupled to the second end of the shiftable member, and
the shiftable member being movable to move the x-ray tray between a lower first position and an elevated second position.

14. The apparatus of claim 13, wherein the x-ray tray, the shiftable member and the two first links form a first parallelogram linkage, and wherein the frame, the shiftable member and the two second links form a second parallelogram linkage.

15. The apparatus of claim 13, wherein the x-ray tray moves only vertically relative to the frame between a lower first position spaced apart from the deck to permit loading of an x-ray cassette on the x-ray tray and an elevated second position located closer to the deck.

16. The apparatus of claim 15, comprising first and second cross members coupled to the frame, the x-ray tray including flanges at opposite ends configured to engage the first and second cross members coupled to the frame to hold the x-ray tray in the same horizontal position relative to the frame during movement of the x-ray tray.

17. The apparatus of claim 13, wherein the deck has a length dimension, and wherein the x-ray tray extends below substantially the entire length dimension of the deck.

18. The apparatus of claim 13, wherein the x-ray tray includes a non-slip top surface for engaging the x-ray cassette.

19. The apparatus of claim 13, including a handle for moving the shiftable member, the handle being movable to a storage position located under the frame.

20. The apparatus of claim 19, wherein the handle is spring-biased to the storage position.

21. The apparatus of claim 13, including a handle pivotably coupled to the frame, the apparatus further comprising a spring having a first end coupled to the handle and a second end coupled to the shiftable member to lift the x-ray tray upwardly to an elevated second position when the handle is rotated relative to the frame from a first storage position to a second x-ray position.

22. The apparatus of claim 21, further comprising a shaft coupled to the handle, and an arm having a first end coupled to the shaft and a second end coupled to the first end of the spring.

23. The apparatus of claim 22, wherein the arm is configured such that rotation of the handle to the second x-ray position moves the arm over center so that the spring biases the x-ray tray toward its elevated second position.

24. The apparatus of claim 13, further comprising a spring coupled between a handle and the shiftable member, the spring being configured to hold the x-ray tray in the elevated second position to bias an x-ray cassette supported on the x-ray tray against a bottom surface of the deck regardless of the thickness of the x-ray cassette supported on the x-ray tray.

25. The apparatus of claim 13, wherein the sum of the distances between the first and second ends of the first and second links of the first pair of links and the sum of the distances between the first and second ends of the first and second links of the second pair of links is each greater than the distance between the deck and the frame so as to enable the lifting apparatus to hold the x-ray cassette against a bottom surface of the deck regardless of the thickness of an x-ray cassette supported on the x-ray tray.

26. A patient support apparatus comprising
a frame,
a patient support deck coupled to the frame,
a tray configured to receive an x-ray cassette, and supported for movement toward the patient support deck,
a shiftable member supported for translation relative to the frame,
at least one linkage including a first link coupled to the tray for pivoting movement about a first axis and a second link coupled to the frame for pivoting movement about a second axis, wherein the first and second links are coupled to the shiftable member for pivoting movement about a third axis that is parallel with and spaced from the first and second axes, and wherein the third axis moves toward a vertical plane defined by first and second axes during translation of the shiftable member to move the tray toward the patient support deck.

27. The patient support apparatus of claim 26, wherein the tray is positioned beneath the patient support deck, and wherein the at least one linkage is movable to raise the tray toward the patient support deck.

28. The patient support apparatus of claim 27, wherein the shiftable member is positioned between the tray and the frame.

29. The patient support apparatus of claim 28, wherein the at least one linkage is also positioned between the tray and the frame.

30. The patient support apparatus of claim 26, further including a handle coupled to the frame, the handle is rotatable relative to the frame to translate the shiftable member relative to the frame.

31. The patient support apparatus of claim 30, wherein the handle is movable to a storage position located under the frame.

32. The patient support apparatus of claim 31, wherein the handle is spring-biased to the storage position.

33. The patient support apparatus of claim 26, further including a first pair of linkages and a second pair of linkages coupled to first and second ends of the shiftable member respectively.

34. The patient support apparatus of claim 26, further including a handle, a shaft coupled to the handle, an arm extending from the shaft, and an extensible element coupled to the arm and coupled to the shiftable member.

35. The patient support apparatus of claim 34, wherein the extensible member includes a spring and a cable coupled to the spring.

36. The patient support apparatus of claim 34, wherein the handle is movable to a storage position located under the frame.

37. The patient support apparatus of claim 36, wherein the handle is spring-biased to the storage position.

38. The apparatus of claim 26, wherein the tray moves only vertically relative to the frame between a lower first position spaced apart from the deck to permit loading of an x-ray cassette on the x-ray tray and an elevated second position located closer to the deck.

39. The apparatus of claim 38, wherein the x-ray tray includes flanges at opposite ends which are configured to engage first and second cross members coupled to the frame to hold the x-ray tray in the same horizontal position relative to the frame during movement of the x-ray tray.

40. The apparatus of claim 26, wherein the deck has a length dimension, and wherein the tray extends below substantially the entire length dimension of the deck.

41. The apparatus of claim 26, wherein the x-ray tray includes a non-slip top surface for engaging the x-ray cassette.

42. The apparatus of claim 26, further including a handle pivotably coupled to the frame and a spring having a first end coupled to the handle and a second end coupled to the shiftable member to lift the x-ray tray upwardly to an elevated second position when the handle is rotated relative to the frame from a first storage position to a second x-ray position.

43. The apparatus of claim 42, further comprising a shaft coupled to the handle, and an arm having a first end coupled to the shaft and a second end coupled to the first end of the spring.

44. The apparatus of claim 43, wherein the arm is configured such that rotation of the handle to the second x-ray position moves the arm over center so that the spring holds the x-ray tray in its elevated second position.

45. The apparatus of claim 26, further including a handle pivotably coupled to the frame and a spring coupled between the handle and the shiftable member, the spring being configured to hold the x-ray tray in an elevated second position to hold the x-ray cassette against a bottom surface of the deck regardless of the thickness of an x-ray cassette supported on the x-ray tray.

46. The apparatus of claim 26, wherein the sum of the distances between the first and third axes and second and third axes is greater than the distance between the deck and the frame so as to enable the lifting apparatus to hold the x-ray cassette against a bottom surface of the deck regardless of the thickness of an x-ray cassette supported on the x-ray tray.

47. A lifting apparatus for an x-ray tray positioned below a patient support deck coupled to a frame, the lifting apparatus comprising:
   a shiftable member supported for translation relative to the frame in a longitudinal direction,
   a pair of links coupled to the shiftable member, a first link of the pair of links having a first end pivotally coupled to the tray and a second end pivotally coupled to the shiftable member, a second link of the pair of links having a first end pivotally coupled to the frame and a second end pivotally coupled to the shiftable member,
   the shiftable member being movable in the longitudinal direction to spread apart the links and lift the tray toward the patient support deck, and
   a handle for moving the shiftable member, the handle being movable to a storage position located under a portion of the frame.

* * * * *